United States Patent [19]

Horino et al.

[11] Patent Number: 4,684,737

[45] Date of Patent: Aug. 4, 1987

[54] PROCESS FOR PRODUCING SUBSTITUTED PHTHALIC ACID COMPOUNDS

[75] Inventors: Hiroshi Horino, Yokohama; Michiro Ohnaka, Kamakura; Atsushi Hayashi, Yokohama; Yoshiko Ikeno, Kawasaki, all of Japan

[73] Assignee: Nippon Zeon Co., Ltd., Tokyo, Japan

[21] Appl. No.: 641,729

[22] Filed: Aug. 17, 1984

[30] Foreign Application Priority Data

Aug. 19, 1983 [JP] Japan ................................ 58-151158

[51] Int. Cl.[4] ................. C07D 307/89; C07C 51/305; C07C 67/28
[52] U.S. Cl. ..................................... 549/240; 549/243; 549/246; 558/416; 560/146; 562/480; 562/471; 562/473
[58] Field of Search ....................... 560/146, 471, 473; 562/480; 260/465 D; 549/240, 246, 243; 558/416

[56] References Cited

U.S. PATENT DOCUMENTS 2,782,221  2/1957  Reed ................................ 562/480 X
4,302,396  11/1981  Tsujimoto et al. ............. 562/480 X

FOREIGN PATENT DOCUMENTS 1493217  10/1969  Fed. Rep. of Germany .
2049636  3/1971  France .

*Primary Examiner*—Natalie Trousof
*Assistant Examiner*—Vera C. Clarke
*Attorney, Agent, or Firm*—Sherman and Shalloway

[57] ABSTRACT

A process for producing a substituted phthalic acid which comprises heating a substituted tetrahydrophthalic acid compound having a substituent in at least one of the 3-, 4-, 5- and 6-positions in the presence of sulfur to dehydrogenate it, and heat-treating the product in the presence of water optionally together with an organic solvent. As required, the heat-treated product is dehydrocyclized to form a substituted phthalic acid anhydride.

13 Claims, No Drawings

PROCESS FOR PRODUCING SUBSTITUTED PHTHALIC ACID COMPOUNDS

This invention relates to an improved process for producing substituted phthalic acid compounds. More specifically, this invention relates to a process for producing a substituted phthalic acid compound which comprises dehydrogenating a substituted tetrahydrophthalic acid compound with sulfur, heating the product with water, and further as required, dehydrocyclizing the product.

In the present specification and the appended claims, the term "substituted phthalic acid compound" generically denotes "substituted phthalic acid" and "substituted phthalic anhydride", and the term "substituted" means "substituted at the aromatic ring".

Substituted phthalic acid compounds such as 4-methylphthalic acid or its anhydride are useful as intermediates for agricultural chemicals and medicines. A conventional process for synthesizing these compounds involves dehydrating the corresponding tetrahydrophthalic acids or the anhydrides thereof. Specific methods proposed so far include (1) a method which comprises heating the starting compound at 150° to 250° C. in the presence of a noble metal catalyst typified by a palladium-carbon catalyst to dehydrogenate it catalytically, (2) a method which comprises subjecting the starting compound to addition reaction with a halogen such as bromine and then heating the adduct at a high temperature to dehydrogenate it, and (3) a method which comprises heating the starting compound with sulfur to dehydrogenate it (DE-A-1,493,217 and FR-A-2,049,636).

The method (1), however, cannot be used in practical applications because it yields great quantities of by-products, such as the product resulting from the hydrogenation of the carbon-carbon double bond of the starting substituted tetrahydrophthalic acid by hydrogen generated by dehydrogenation, the product resulting from the shifting of the position of the carbon-carbon double bond of the substituted tetrahydrophthalic acid compound, and the benzoic acid derivative generated by decarboxylation.

The method (2) is known to give the product of a high purity in a relatively high yield. But because it requires a large amount of expensive bromine, and a large amount of hydrogen bromide generated by dehydrobromination must be disposed of, it has not proved to be entirely satisfactory for industrial practice.

The method (3) is most economical because it only needs a small amount of inexpensive sulfur. Investigations of the present inventors, however, have shown that since according to this method, hydrogen sulfide formed by dehydrogenation reacts with the final desired product to form thiophthalic anhydride, the yield of the desired product is reduced and moreover, this by-product is difficult to separate even by recrystallization or distillation.

The present inventors have made investigations in order to remedy the defect of the method (3). These investigations have led to the discovery that by heat-treating the dehydrogenation product in the presence of water, the yield of the final desired product can be greatly increased, and the purification of the final product is made very easy.

Thus, according to this invention, there is provided a process for producing a substituted phthalic acid compound, which comprises heating a substituted tetrahydrophthalic acid compound having a substituent in at least one of the 3-, 4-, 5- and 6-positions in the presence of sulfur to dehydrogenate it and heat-treating it in the presence of water to obtain a substituted phthalic acid, or dehydrocyclizing the substituted phthalic acid to obtain a substituted phthalic anhydride.

The substituted tetrahydrophthalic acid compound used as a starting material in this invention is one which can be converted to the corresponding substituted phthalic acid compound by dehydrogenation, namely one having a substituent in at least one of the 3-, 4-, 5- and 6-positions. Specific examples of the substituent are lower alkyl groups, lower alkoxy groups, acyloxy groups, a cyano group, a phenyl group or halogens.

Specific examples of the substituted tetrahydrophthalic acid compound include 4-methyl-1,2,3,6-tetrahydrophthalic acid, 3-methyl-1,2,3,6-tetrahydrophthalic acid, 4,5-dimethyl-1,2,3,6-tetrahydrophthalic acid, 3,4-dimethyl-1,2,3,6-tetrahydrophthalic acid, 3,5-dimethyl-1,2,3,6-tetrahydrophthalic acid, 3,6-dimethyl-1,2,3,6-tetrahydrophthalic acid, 4-ethyl-1,2,3,6-tetrahydrophthalic acid, 4-propyl-1,2,3,6-tetrahydrophthalic acid, 4-isopropyl-1,2,3,6-tetrahydrophthalic acid, 4-butyl-1,2,3,6-tetrahydrophthalic acid, 4-methoxy-1,2,3,6-tetrahydrophthalic acid, 4-acetoxy-1,2,3,6-tetrahydrophthalic acid, 4-phenyl-1,2,3,6,-tetrahydrophthalic acid, 4-cyano-1,2,3,6-tetrahydrophthalic acid, 4-methyl-1,2,5,6-tetrahydrophthalic acid, 4-methyl-1,4,5,6-tetrahydrophthalic acid and 4-methyl-3,4,5,6-tetrahydrophthalic acid, and anhydrides of these acids. Lower alkyl-substituted compounds, particularly lower alkyl-substituted-1,2,3,6-tetrahydrophthalic anhydrides, are preferred because raw materials for these compounds are readily available and these compounds have good reactivity.

The amount of sulfur used in the reaction may be chosen properly. Usually, it is 1 to 10 gram-atoms, preferably 1.5 to 5 gram-atoms, more preferably 1.8 to 2.5 gram-atoms, per mole of the substituted tetrahydrophthalic acid compound. If the amount of sulfur used is excessively small, the yield of the final product is decreased, and the purification and quality of the desired product are adversely affected. If it is too large, the sulfur content in the waste material increases so that the after-treatment of the waste material becomes complex.

The manner of feeding sulfur in the reaction is not particularly restricted. For example, it may be charged from the outset together with the substituted tetrahydrophthalic acid compound, or feeding them continuously or intermittently as the reaction proceeds.

The other conditions for dehydrogenation can be selected properly in accordance with a customary method. The reaction temperature is usually 180° to 350° C., preferably 200° to 300° C., and the reaction time is 5 minutes to 5 hours, preferably 20 minutes to 3 hours. The reaction is usually carried out in the absence of a solvent. As required, a high-boiling solvent inert to the reaction may be used.

After the dehydrogenation of the substituted tetrahydrophthalic acid, the product is heat-treated in the presence of water and optionally an organic solvent. The amount of water used can be selected properly. Usually, it is 0.3 to 20 parts by weight, preferably 0.8 to 5 parts by weight, per part by weight of the reaction product. If the amount of water is too small, the effect of improving the yield is reduced.

Specific examples of the organic solvent which is used as required are benzene, toluene, xylene, ethylbenzene, cumene, heptane, octane, decane, tetrahydrofuran, and carbon tetrachloride. Of these, the aromatic hydrocarbons are preferred. The amount of the organic solvent can be selected properly. Usually, it is not more than 0.1 part by weight, preferably 0.005 to 0.05 part by weight, per part by weight of the reaction product. The use of the organic solvent makes it possible to prevent blockage of the apparatus during heat-treatment and stabilize the operation.

The heat-treatment can be carried out immediately after the dehydrogenation reaction. If the subsequent purification step is considered, however, it is desirable to first distill the dehydrogenation product to remove high-boiling by-products and then heat-treat the product.

The heat-treatment is carried out usually at a temperature of 50° to 200° C. for 0.5 to 20 hours, preferably at 90° to 150° C. for 1 to 10 hours. In order to increase the yield of the final product, it is desirable to perform the heat-treatment while removing hydrogen sulfide generated during the heat-treatment. A specific procedure for removing hydrogen sulfide is, for example, to remove it while it is entrained in steam, or to remove it out of the system by blowing an inert gas such as air and nitrogen into the reaction vessel.

By this heat-treatment according to the process of this invention, a large amount of a substituted thiophthalic anhydride contained in the reaction product can be converted efficiently into a substituted phthalic acid.

The resulting substituted phthalic acid can be recovered by customary methods. Specifically, it can be carried out by a method which comprises heating the aqueous solution resulting from the heat-treatment together with an organic solvent capable of forming an azeotrope with water, thereby removing water as an azeotrope with the organic sovlent, a method which comprises heating the aqueous solution to evaporate water to dryness, or a method which comprises drying the aqueous solution under reduced pressure.

As required, the substituted phthalic acid so produced may be dehydrocyclized to give the corresponding substituted phthalic anhydride. The dehydrocyclization reaction may be carried out in a customary manner. Specific examples include a method which involves heating the substituted phthalic acid at a high temperature of 100° to 300° C., a method comprising heating it with a solvent capable of forming an azeotrope with water and removing water as an azeotrope with the solvent, or a method comprising treating it with a dehydrating agent such as acetic anhydride or thionyl chloride.

The resulting substituted phthalic anhydride may be recovered in a customary manner. For example, this can be effected by recrystallization from a solvent, or by distillation.

Thus, according to this invention, by using an inexpensive material and performing a simple operation, the desired substituted phthalic acid compound can be obtained in good yields.

The following examples illustrate the present invention more specifically. All parts and percentages in these examples are by weight unless otherwise specified.

COMPARATIVE EXAMPLE 1

A flask equipped with a reflux condenser was charged with 23.4 parts of 4-methyl-1,2,3,6-tetrahydrophthalic anhydride and 9.0 parts of sulfur, and they were reacted at 230° to 250° C. for 1 hour to obtain a brackish brown tarry reaction product. The reaction product was distilled by a kugelrohr under reduced pressure generated by an aspirator to give 18.7 parts of a distillate.

Analysis showed the distillate to contain about 65% of 4-methylphthalic anhydride and 31% of 4-methylthiophthalic anhydride. The two components were difficult to separate even by repeated recrystallization from a mixture of benzene and methylcyclohexane.

EXAMPLE 1

Dehydrogenation reaction and distillation were carried out in the same way as in Comparative Example 1. The distillate (18.7 parts) and 60 parts of distilled water were charged into a flask equipped with a reflux condenser and refluxed for 2 hours to remove the generated hydrogen sulfide out of the flask. The resulting yellow clear aqueous solution was distilled under reduced pressure to remove water and to give 19.5 parts of 4-methylphthalic acid.

EXAMPLE 2

4-Methylphthalic acid was synthesized in the same way as in Example 1, and then dehydrated at 180° to 200° C. The dehydrated product was then recrystallized from a mixture of 17 parts of benzene and 34 parts of methylcyclohexane to give 14.6 parts of 4-methylphthalic anhydride as crystals having a melting point of 92.5° C.

EXAMPLE 3

The procedure of Example 2 was repeated except that 3-methyl-1,2,3,6-tetrahydrophthalic anhydride was used instead of 4-methyl-1,2,3,6-tetrahydrophthalic anhydride. There was obtained 13.2 parts of 3-methylphthalic anhydride as needlelike crystals having a melting point of 116.9° C.

EXAMPLE 4

The procedure of Example 2 was repeated except that 4-methyl-3,4,5,6-tetrahydrophthalic anhydride was used instead of 4-methyl-1,2,3,6-tetrahydrophthalic anhydride. There was obtained 13.5 parts of 4-methylphthalic anhydride having a melting point of 92.0° C.

EXAMPLE 5

Dehydrogenation reaction and distillation were carried out in the same way as in Comparative Example 1. The resulting distillate (18.7 parts) and 18.7 parts of distilled water were charged into a flask equipped with a reflux condenser, and refluxed for 6 hours to remove the generated hydrogen sulfide out of the flask. The resulting yellow clear aqueous solution was heated under reduced pressure to concentrate it to about half of the original volume. Then, 20 parts of xylene was added, and the mixture was heated to above 100° C. to remove water as an azeotrope with xylene. The residue was worked up in the same way as in Example 2 to give 15.0 parts of 4-methylphthalic anhydride as crystals.

EXAMPLE 6

Example 5 was repeated except that the heattreatment of the dehydrogenation reaction product was carried out in the presence of 18.7 parts of distilled water and 0.5 part of xylene. During the heat-treatment, no material was seen to adhere to the flask or the reflux condenser. There was obtained 15.2 parts of 4-methylphthalic anhydride as crystals.

What is claimed is:

1. A process for producing a substituted phthalic acid, which comprises heating a substituted terahydrophthalic acid compound having a substituent selected from the group consisting of lower alkyl, lower alkoxy, acyloxy, cyano, phenyl and halogen in at least one of the 3-, 4-, 5-and 6-positions at a temperature of 180°–350° C. in the presence of one to ten gram-atoms per mole of said compound of sulfur to dehydrogenate it and, subsequently, heat-treating the dehydrogenation product at a temperature of 50° to 200° C. in the presence of 0.3 to 20 parts by weight of water per part by weight by the dehydrogenation product.

2. The process of claim 1 wherein the dehydrogenation reaction is carried out for from 5 minutes to 5 hours.

3. The process of claim 1 wherein the heat-treatment is carried out for from 0.5 to 20 hours.

4. The process of claim 1 wherein the heat-treatment is carried out in the further presence of an organic solvent.

5. The process of claim 4 wherein the organic solvent is an aromatic hydrocarbon.

6. The process of claim 1 wherein the amount of sulfur present is 1.5 to 5 gram-atoms, per mole of the substituted tetrahydrophthalic acid compound.

7. The process of claim 1 wherein the amount of water is 0.8 to 5 parts by weight per part by weight of the dehydrogenation product.

8. The process of claim 4 wherein the organic solvent is present in an amount of not more than 0.1 part by weight, per part by weight of the dehydrogenation product.

9. The process of claim 1 further comprising the step of distilling the dehydrogenation product prior to heat treating.

10. The process of claim 4 wherein the organic solvent is selected from the group consisting of benzene, toluene, xylene, ethylbenzene, cumene, heptane, octane, decane, tetrahydrofuran and carbon tetrachloride.

11. The process of claim 1 wherein the substituent is lower alkyl.

12. A process for producing a substituted phthalic anhydride which comprises heating a substituted tetrahydrophthalic compound having a substituent selected from the group consisting of lower alkyl, lower alkoxy, acyloxy, cyano, phenyl and halogen in at least one of the 3-, 4-, 5- and 6-positions at a temperature of 180°–350° C. in the presence of 1 to 10 gram-atoms per mole of said compound of sulfur to dehydrogenate it, heat-treating the dehydrogenation product at a temperature of 50° to 200° C. in the presence of 0.3 to 20 parts by weight of water per part by weight of dehydrogenation product to produce a substituted phthalic acid, and then dehydrocyclizing the substituted phthalic acid to form a substituted phthalic anhydride.

13. The process of claim 12 wherein the dehydrocyclization reaction is carried out by heating.

* * * * *